(12) United States Patent
Katsuki et al.

(10) Patent No.: US 8,410,295 B2
(45) Date of Patent: Apr. 2, 2013

(54) METHOD FOR PRODUCTION OF OPTICALLY ACTIVE EPOXY COMPOUND, AND COMPLEX USED THEREFOR AND PROCESS FOR PRODUCING THE SAME

(75) Inventors: Tsutomu Katsuki, Fukuoka (JP); Kazuhiro Matsumoto, Fukuoka (JP); Yuji Sawada, Fukuoka (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/426,186

(22) Filed: Mar. 21, 2012

(65) Prior Publication Data

US 2012/0178954 A1 Jul. 12, 2012

Related U.S. Application Data

(62) Division of application No. 11/795,149, filed as application No. PCT/JP2005/023962 on Dec. 27, 2005, now Pat. No. 8,163,941.

(30) Foreign Application Priority Data

Feb. 18, 2005 (JP) .................................. 2005-42320

(51) Int. Cl.
*C07F 7/28* (2006.01)
(52) U.S. Cl. ........................................................ 556/56
(58) Field of Classification Search ................. 556/56
See application file for complete search history.

(56) References Cited

U.S. PATENT DOCUMENTS 6,054,065 A 4/2000 Uang et al.
6,160,138 A 12/2000 Escrig et al.

FOREIGN PATENT DOCUMENTS

| JP | A-11-335384 | 12/1999 |
| JP | A-2002-308845 | 10/2002 |
| TW | 434207 B | 5/2001 |
| TW | 499410 B | 8/2002 |

OTHER PUBLICATIONS

PCT International Preliminary Report on Patentability, issued Aug. 21, 2007.*
Colonna, S. et al., "Highly Enantioselective Epoxidation by Means of Polyaminoacids in a Triphase System: Influence of Structural Variations Within the Catalysts," Synthetic Enzymes-4[1], Tetrahedron, 1983, pp. 1635-1641, vol. 39, No. 9, Pergation Press Ltd., Great Britain.
Feb. 14, 2006 International Search Report issued in International Application No. PCT/JP2005/023962.
Jacobsen, E. et al., "Epoxidation of Alkenes Other than Allylic Alcohols," Comprehensive Asymmetric Catalysts, 1999, pp. 649-677, vol. II, Chapter 18.2.
Katsuki, T. et al., "The First Practical Method for Asymmetric Epoxidation," *J. Am. Chem. Soc.*, 1980, pp. 5974-5976, vol. 102, American Chemical Society.
Katsuki, T., "Metal Complexes as Catalysts for Oxygen, Nitrogen, and Carbon-Atom Transfer Reactions," Comprehensive Coordination Chemistry II, 2003, pp. 207-251, vol. 9, Chapter 9.4, Elsevier Science Ltd., Oxford.
Mar. 18, 2011 Decision of Rejection issued in Chinese Application No. 200580042857.9 (with translation).
Matsumoto, K. et al., "Construction of a Psuedo-Heterochiral and Homochiral Di-μ-oxotitanium (Schiff Base) Dimers and Enantioselective Epoxidation Using Aqueous Hydrogen Peroxide," Angewandte Chemie, 2005, pp. 4935-4939, vol. 44, No. 31, Wiley-VCH Verlag GmbH & Co. KgaA, Welnheim.
Matsumoto, K. et al., "Enantioselective Epoxidation Using Self-assembled Dinuclear Titanium Complex," The Chemical Society of Japan, Mar. 2005, p. 1102, vol. 85, No. 2.
Saito, B. et al., "Ti(salen)-Catalyzed Enantioselective Sulfoxidation Using Hydrogen Peroxide as a Terminal Oxidant," Tetrahedron Letters, 2001, pp. 3873-3876, vol. 42, Elsevier Science Ltd.
Shu, L. et al., "An Efficient Ketone-Catalyzed Asymmetric Epoxidation Using Hydrogen Peroxide ($H_2O_2$) as Primary Oxidant," Tetrahedron, 2001, pp. 5213-5218, vol. 57, Elsevier Science Ltd.
Ward, C. V. et al., "New Chiral Catalysts for Phospho-Transfer," Tetrahedron Letters, 2000, pp. 6181-6184, vol. 41, Elsevier Science Ltd.

* cited by examiner

*Primary Examiner* — Porfirio Nazario Gonzalez
(74) *Attorney, Agent, or Firm* — Oliff & Berridge, PLC

(57) ABSTRACT

A complex, and a process for producing the same, represented by any of the following formulae (I), (I'), (II), (II'), (III), (III'), (IV), and (IV'):

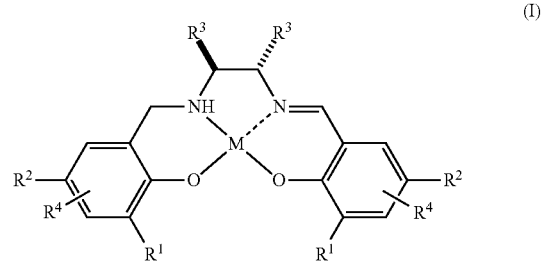

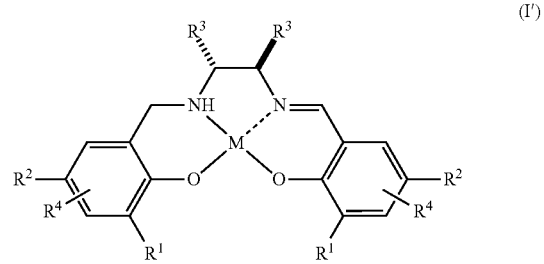

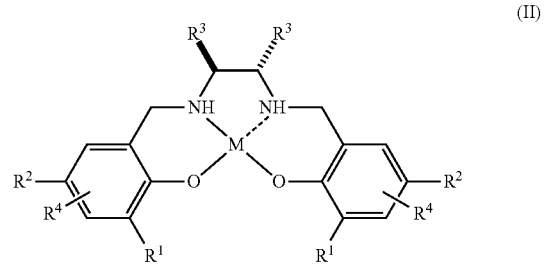

-continued

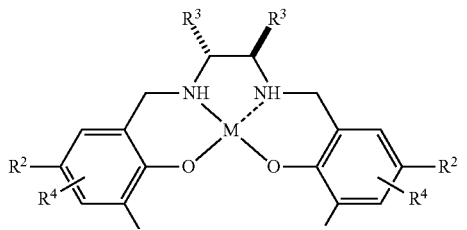
(II')

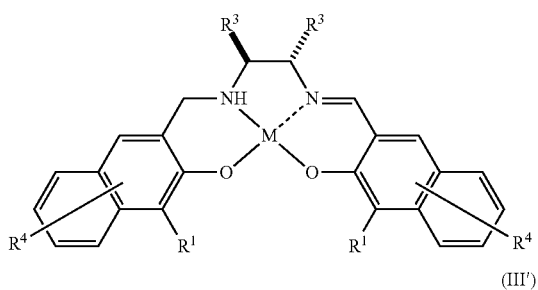
(III)

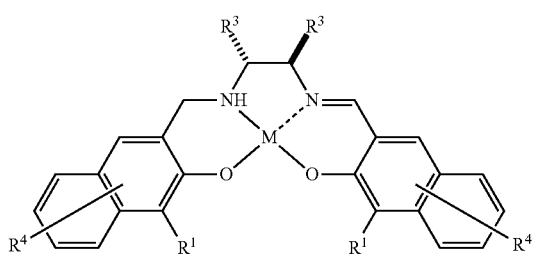
(III')

-continued

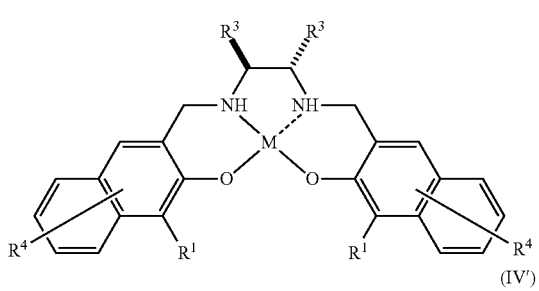
(IV)

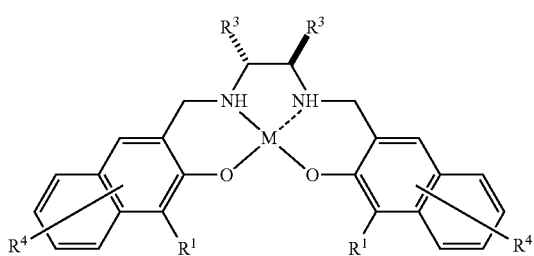
(IV')

where: $R^1$s are independently an alkyl group or an aryl group; $R^2$s are independently a hydrogen atom, an alkyl group, or an aryl group; $R^3$s are independently an alkyl group or an aryl group, provided that two $R^3$s are optionally bonded with each other to form a ring; $R^4$s are independently a hydrogen atom, a halogen atom, an alkyl group, an alkoxy group, a nitro group, or a cyano group; and M is $TiY_2$, where Y is Cl or alkoxide or the complex forms a di-µ-oxo dimer where Y is a µ-oxo ligand.

13 Claims, No Drawings

METHOD FOR PRODUCTION OF OPTICALLY ACTIVE EPOXY COMPOUND, AND COMPLEX USED THEREFOR AND PROCESS FOR PRODUCING THE SAME

This is a Divisional Application of application Ser. No. 11/795,149 filed Jul. 12, 2007, which is a National Stage of Application No. PCT/JP2005/023962 filed Dec. 27, 2005, which claims priority to Japanese Patent Application No. 2005-042320 filed Feb. 18, 2005. The prior applications, including the specifications, drawings and abstracts are incorporated herein by reference in their entirety.

TECHNICAL FIELD

The present invention relates to a method for producing an optically active epoxy compound as well as a complex used herefore and a process for producing the same, and more particularly to a method for producing an optically active epoxy compound by subjecting a prochiral compound having a carbon-carbon double bond in its molecule to an asymmetric epoxidation using a Ti complex with a specific structure as a catalyst.

BACKGROUND ART

The optically active epoxy compounds are widely used as an intermediate for various drugs including optically active benzopyran compounds effective for the treatment of hypertension, asthma and so on, and various methods for the synthesis of the optically active epoxy compounds have been widely examined. Among such synthesis methods, an asymmetric epoxidation is the most practical method, and since the discovery of asymmetric epoxidation using titanium tartrate as a catalyst (see T. Katsuki, K. B. Sharpless, J. Am. Chem. Soc. 1980, 102, 5974-5976), various synthesis methods using the asymmetric epoxidation have been developed (see E. N. Jacobsen, M. H. Wu, In "Comprehensive Asymmetric Catalysis" Ed. By Jacobsen, E. N.; Pfaltz, A.; Yamamoto, H. Springer (1999), Vol. II, Chap. 18.2, pp. 649-677. and T. Katsuki, In "Comprehensive Coordination Chemistry II" Ed. By McCleverty, J., Elsevier Science Ltd., Oxford, 2003, Vol. 9, Chapter 9.4, pp. 207-264).

However, many of these synthesis methods use an oxidant having a low atomic efficiency such as t-butyl hydroperoxide, hypochlorite, iodosobenzene or the like, so that it is strongly demanded to develop synthesis methods using an oxidant having a higher atomic efficiency and being environmentally benign. Among various oxidants, hydrogen peroxide is an environmentally benign oxidant because the atomic efficiency is high but also only water is produced after the transition of oxygen atom. For this end, asymmetric epoxidation using hydrogen peroxide as an oxidant has been studied vigorously, but there are very few eases where epoxidation could be attained with a high enantioselectivity (see L. Shu, Y. Shi, Tetrahedron, 2001, 57, 5213-5218. and S. Colonna, H. Molinari, S. Banfi, S. Julia, J. Masana, A. Alvalez, Tetrahedron, 1983, 39, 1635-1641). In many cases, there is a problem that the turnover number of the catalyst is insufficient.

On the other hand, the inventors have already discovered that (Arr Δ, Arr Δ)-di-μ-oxo Ti(salen) complex is exceptional as a catalyst for asymmetric sulfonation using urea-hydrogen peroxide adduct (UHP) as the oxidant (see B. Saito, T. Katsuki, Tetrahedron Lett., 2001, 42, 3873-3876). However, although the above (Arr Δ, Arr Δ)-di-μ-oxo Ti(salen) complex is good for oxidizing various sulfide compounds with a high enantioselectivity, it cannot promote the epoxidation of olefins.

DISCLOSURE OF INVENTION

Under these circumstances, it is an object of the present invention to solve the problems of the conventional techniques and to provide an industrially useful method for producing an optically active epoxy compound, and a complex used as a catalyst in this process. Also, it is another object of the present invention to provide a novel process for producing the above complex.

The inventors have made various studies for achieving the above objects and discovered that it is possible to promote the epoxidation of olefins using hydrogen peroxide as an oxidant with a high enantioselectivity by using as a catalyst di-μ-oxo titanium complex which is obtained by reducing at least one of the two imino bonds within its salen ligand in a reaction system and then self-assembling, and further the turnover number of the catalyst is very high, and as a result, the present invention has been accomplished.

That is, the method for producing an optically active epoxy compound according to the present invention is characterized in that a complex represented by any of the following formulae (I), (I'), (II), (II'), (III), (III'), (IV), and (IV'):

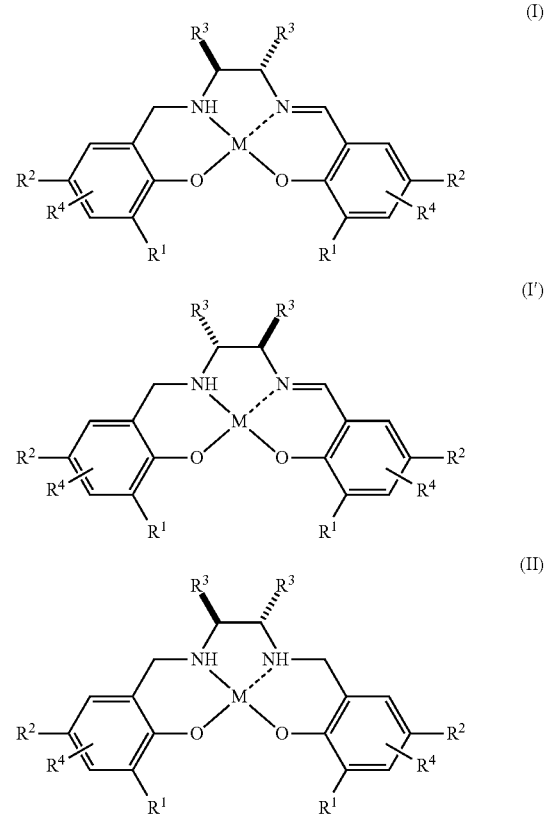

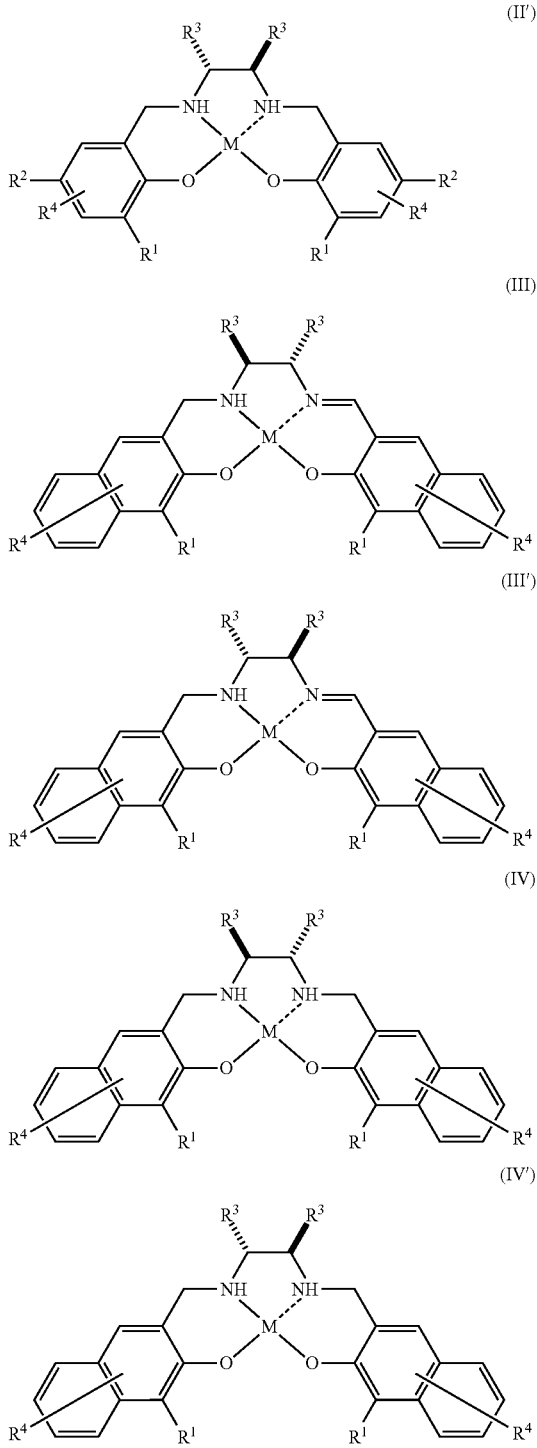

[wherein R¹s are independently an alkyl group or an aryl group; R²s are independently an alkyl group or an aryl group; R³s are independently an alkyl group or an aryl group, provided that two of R³s may be bonded with each other to form a ring; R⁴s are independently a hydrogen atom, a halogen atom, an alkyl group, an alkoxy group, a nitro group or a cyano group; M is TiY₂ (wherein Y is Cl or alkoxide or μ-oxo ligand)] (a single substance represented by the above formula or a di-μ-oxo-dimer derived therefrom) is used as a catalyst, and an unsaturated compound represented by the following formula (V):

[wherein each of $R^5$ and $R^6$ is a different monovalent group or a hydrogen atom] is subjected to an asymmetric epoxidation with an oxidant to produce an optically active epoxy compound represented by the following formula (VI):

[wherein $R^5$ and $R^6$ are the same as mentioned above].

In a preferable embodiment of the method for producing an optically active epoxy compound according to the present invention, two of R³s in the above formulae are bonded with each other to form a tetramethylene group.

In another preferable embodiment of the method for producing an optically active compound according to the present invention, the complex is represented by the formula (II), (II'), (III), or (III').

In the other preferable embodiment of the method for producing an optically active compound according to the present invention, R¹ in the above formulae is 2-aryl-1-naphthyl group or phenyl group.

In a further preferable embodiment of the method for producing an optically active compound according to the present invention, said Y is a μ-oxo ligand. In this case, the complex represented by any of the above formulae (I), (I'), (II), (II'), (III), (III'), (IV), and (IV') is a titanium binuclear complex.

In another preferable embodiment of the method for producing an optically active compounds according to the present invention, the unsaturated compound represented by the formula (V) is represented by any of the following formulae (VII), (VIII), and (IX):

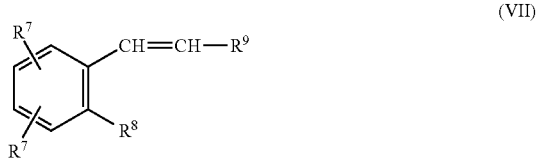

[wherein R⁷s are independently a hydrogen atom, a cyano group, a nitro group, an amino group which may be protected with a protection group, a halogen atom, an alkyl group, an alkoxy group, a halogenoalkyl group, a carboxy group, a formyl group, an alkanoyl group, an aroyl group, a halogenoalkanoyl group, a carbamoyl group, an alkylsulfinyl group, an arylsulfinyl group, an alkylsulfonyl group, an arylsulfonyl group, an aminosulfonyl group, or a mono- or di-alkylaminosulfonyl group; R⁸ is a hydrogen atom, an alkyl group, or an alkoxy group; R⁹s are independently a hydrogen atom, an alkyl group, an alkoxy group, a phenyl group, or a substituted phenyl group substituted with a halogen atom, an alkyl group, or an alkoxy group, provided that R⁹s in the formula (IX) are different from each other; R⁸ and R⁹ in the formula (VII) may be bonded with each other to form a bivalent group represented by any of the following formulae (X), (XI), (XII), and (XIII):

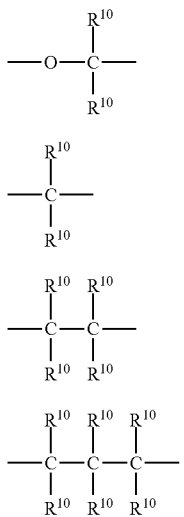

(X)

(XI)

(XII)

(XIII)

(wherein $R^{10}$s are independently a hydrogen atom or an alkyl group)], and the resulting optically active epoxy compound is represented by any of the following formulae (XIV), (XV), and (XVI):

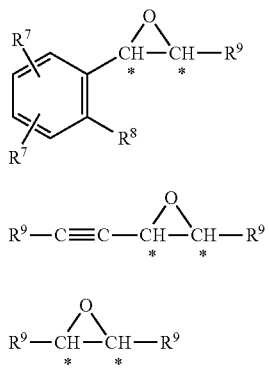

(XIV)

(XV)

(XVI)

[wherein $R^7$, $R^8$, and $R^9$ are the same as mentioned above, provided that $R^9$s in the formula (XVI) are different from each other, and $R^8$ and $R^9$ in the formula (XIV) may be bonded with each other to form a bivalent group represented by any of the above formulae (X), (XI), (XII), and (XIII)].

In the other preferable embodiment of the method for producing an optically active compound according to the present invention, the oxidant is aqueous hydrogen peroxide or urea-hydrogen peroxide adduct (UHP), and it is more preferable that the oxidant is aqueous hydrogen peroxide. In this case, the atomic efficiency of the oxidant is high but also the by-product after the epoxidation is harmless, so that an environmentally benign process can be achieved.

Also, the complex according to the present invention is characterized by being represented by any of the above formulae (I), (I'), (II), (II'), (III), (III'), (IV), and (IV').

In the complex according to the present invention, it is preferable that the two $R^3$s in the aforementioned formulae are bonded with each other to form a tetramethylene group, that $R^1$ in the aforementioned formulae is 2-aryl-1-naphthyl group or phenyl group, and that the aforementioned Y is μ-oxo ligand. Also, as the complex according to the present invention are preferable the complexes represented by the above formulae (II), (II'), (III), and (III').

Furthermore, the first production process for the complex according to the present invention is characterized in that a salen ligand represented by any of the following formulae (XVII), (XVII'), (XVIII), and (XVIII'):

(XVII)

(XVII')

(XVIII)

(XVIII')

[wherein $R^1$, $R^2$, $R^3$, $R^4$ are the same as mentioned above] is reacted with titanium alkoxide and then treated with water to produce a complex represented by any of the above-mentioned formulae (I), (I'), (III), and (III') in which M is $TiY_2$ (wherein Y is a μ-oxo ligand). Moreover, the complex represented by the formula (I) can be produced by using the salen ligand represented by the formula (XVII), and the complex represented by the formula (I') can be produced by using the salen ligand represented by the formula (XVII'), and the complex represented by the formula (III) can be produced by using the salen ligand represented by the formula (XVIII), and the complex represented by the formula (III') can be produced by using the salen ligand represented by the formula (XVIII').

In the first production process of the complex according to the present invention, it is preferable that the two $R^3$s in the aforementioned formulae are bonded with each other to form a tetramethylene group, and that $R^1$ in the aforementioned formulae is 2-aryl-1-naphthyl group.

In a preferable embodiment of the first production process of the complex according to the present invention, the salen ligand is represented by the formula (XVIII) or (XVIII') and the complex is represented by the formula (III) or (III').

Furthermore, the second production process of the complex according to the present invention is characterized in that a salen ligand represented by any of the above formulae (XVII), (XVII'), (XVIII), and (XVIII') is reduced to form a salan ligand represented by any of the following formulae (XIX), (XIX'), (XX), and (XX'):

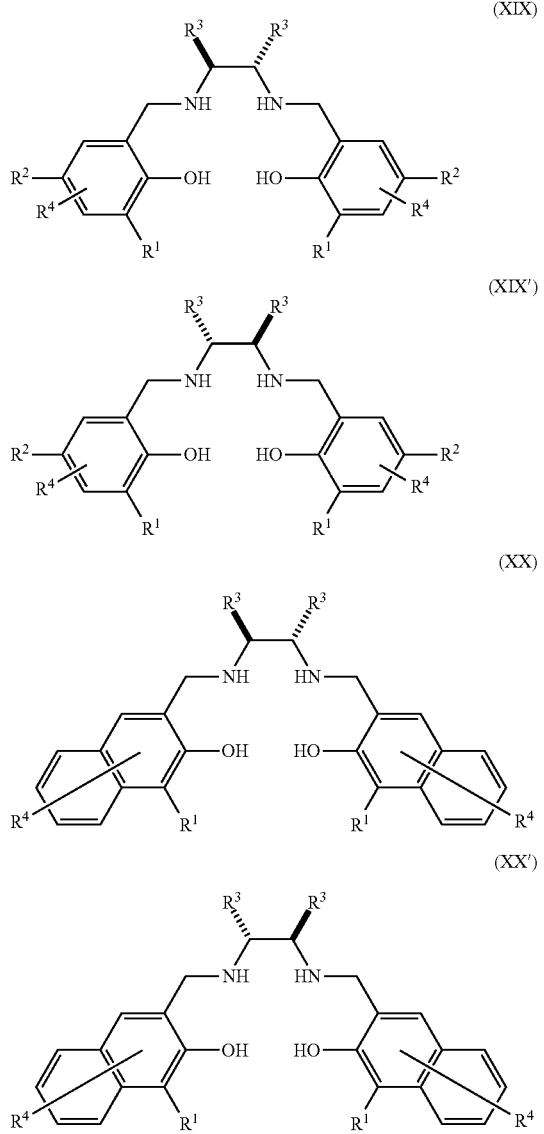

[wherein $R^1$, $R^2$, $R^3$, $R^4$ are the same as mentioned above], and the salan ligand is reacted with titanium alkoxide and then treated with water to produce a complex represented by any of the above-mentioned formulae (II), (II'), (IV), and (IV') in which M is $TiY_2$ (wherein Y is a μ-oxo ligand). Moreover, the complex represented by the formula (II) can be produced by using the salen ligand represented by the formula (XVII) and going through the salan ligand represented by the formula (XIX), and the complex represented by the formula (II') can be produced by using the salen ligand represented by the formula (XVII') and going through the salan ligand represented by the formula (XIX'), and the complex represented by the formula (IV) can be produced by using the salen ligand represented by the formula (XVIII) and going through the salan ligand represented by the formula (XX), and the complex represented by the formula (IV') can be produced by using the salen ligand represented by the formula (XVIII') and going through the salan ligand represented by the formula (XX').

In the second production process of the complex according to the present invention, it is preferable that the two $R^3$s in the aforementioned formulae are bonded with each other to form a tetramethylene group, and that $R^1$ in the aforementioned formulae is a phenyl group.

In a preferable embodiment of the second production process of the complex according to the present invention, the salen ligand is represented by the formula (XVII) or (XVII'), and the salan ligand is represented by the formula (XIX) or (XIX'), and the complex is represented by the formula (II) or (II').

According to the present invention, it is possible to produce an optically active epoxy compound by using a Ti complex represented by the specified structural formula as a catalyst and asymmetrically epoxidizing a prochiral unsaturated compound having a carbon-carbon double bond in its molecule with a high enantioselectivity.

BEST MODE FOR CARRYING OUT THE INVENTION

The present invention will be explained in detail below. The titanium complex used as a catalyst in the present invention is represented by any of the above formulae (I), (I'), (II), (II'), (III), (III'), (IV), and (IV'). The ligand in these complexes has a structure in which at least one of the two imino bonds within the salen ligand is reduced, and is superior in the flexibility to the salen ligand. Also, it is considered that hydrogen bonded to the nitrogen atom in the ligand of the complex can contribute to the activation of the peroxo species of titanium. And, it is considered that the asymmetric epoxidation of the unsaturated compound can be promoted by using the above complex as a catalyst due to the characteristics of these ligands. At this moment, the complex of the formula (I') is an enantiomer of the complex of the formula (I), and the complex of the formula (II') is an enantiomer of the complex of the formula (II), and the complex of the formula (III') is an enantiomer of the complex of the formula (III), and the complex of the formula (IV') is an enantiomer of the complex of the formula (IV), which can be synthesized in the same way by selecting the configuration of the starting material. Among them, the complexes represented by formula (III) and (III') are preferable. The amount of the complex used is preferably within a range of 0.01-100 mol %, more preferably within a range of 0.1-5 mol % based on the molar quantity of the unsaturated compound as a substrate mentioned later.

$R^1$s in the above formulae are independently an alkyl group or an aryl group. As the alkyl group are mentioned alkyl groups having a carbon number of 1-4 such as methyl group, ethyl group, n-propyl group, i-propyl group, n-butyl group, i-butyl group, s-butyl group, t-butyl group and the like, while as the aryl group are mentioned aryl groups having a carbon number of 6-22 such as phenyl group, 3,5-dimethylphenyl group, 4-methylphenyl group, 1-naphthyl group, 2-biphenyl group, 2-phenyl-1-naphthyl group, 2-methyl-1-naphthyl group, 2-[3,5-dimethylphenyl]-1-naphthyl group, 2-[4-methylphenyl]-1-naphthyl group, 2-methoxy-1-naphthyl group, 2-[p-(t-butyldimethylsilyl)phenyl]-1-naphthyl group, 2-biphenylyl-1-naphthyl group and the like. Moreover, the aryl group may be optically active or may be optically inactive. As $R^1$ is preferable phenyl group or 2-aryl-1-naphtyl group, and as the aryl group in 2-aryl-1-naphtyl group are mentioned phenyl group, p-(t-butyldimethylsilyl)phenyl group, biphenylyl group and the like.

Also, $R^2$s in the above formulae are independently an alkyl group or an aryl group. As the alkyl group are mentioned alkyl groups having a carbon number of 1-4 such as methyl group, ethyl group, n-propyl group, i-propyl group, n-butyl group, i-butyl group, s-butyl group, t-butyl group and the like, while as the aryl group are mentioned aryl groups having a carbon number of 6-18 such as phenyl group, 3,5-dimethylphenyl group, 4-methylphenyl group, 1-naphthyl group, 2-biphenyl group, 2-phenyl-1-naphthyl group, 2-methyl-1-naphthyl group, 2-[3,5-dimethylphenyl]-1-naphthyl group, 2-[4-methylphenyl]-1-naphthyl group, 2-methoxy-1-naphthyl group and the like.

In addition, $R^3$s in the above formulae are independently an alkyl group or an aryl group, provided that the two $R^3$s may be bonded with each other to form a ring. As the alkyl group are mentioned alkyl groups having a carbon number of 1-4 such as methyl group, ethyl group, n-propyl group, i-propyl group, n-butyl group, i-butyl group, s-butyl group, t-butyl group and the like, while as the aryl group are mentioned aryl groups having a carbon number of 6-18 such as phenyl group, 3,5-dimethylphenyl group, 4-methylphenyl group, 1-naphthyl group, 2-biphenyl group, 2-phenyl-1-naphthyl group, 2-methyl-1-naphthyl group, 2-[3,5-dimethylphenyl]-1-naphthyl group, 2-[4-methylphenyl]-1-naphthyl group, 2-methoxy-1-naphthyl group and the like. Also, when the two $R^3$s are bonded with each other to form a ring, the resulting bivalent group includes tetramethylene group and the like. Among them, it is preferable that the two $R^3$s are bonded with each other to form a tetramethylene group.

Moreover, $R^4$s in the above formulae are independently a hydrogen atom, a halogen atom, an alkyl group, an alkoxy group, a nitro group or a cyano group. As the halogen atom are mentioned fluorine atom, chlorine atom, bromine atom and the like, and as the alkyl group are preferable alkyl groups having a carbon number of 1-4 such as methyl group, ethyl group, n-propyl group, i-propyl group, n-butyl group, i-butyl group, sec-butyl group, t-butyl group and the like, and as the alkoxy group are preferable alkoxy groups having a carbon number of 1-4 such as methoxy group, ethoxy group, n-propoxy group, i-propoxy group, n-butoxy group, i-butoxy group, sec-butoxy group, t-butoxy group and the like. Among them, the hydrogen atom is especially preferable as $R^4$.

Furthermore, M in the above formulae is $TiY_2$, wherein Y is Cl, an alkoxide or a μ-oxo ligand. As the alkoxide are mentioned methoxide, ethoxide, n-propoxide, i-propoxide, n-butoxide, i-butoxide, s-butoxide, t-butoxide and so on. Also, when Y is a μ-oxo ligand, the above complex is a titanium binuclear complex. As such a titanium binuclear complex is preferable a (Δ, Δ)-di-μ-oxo titanium binuclear complex represented by the following formula (XXI):

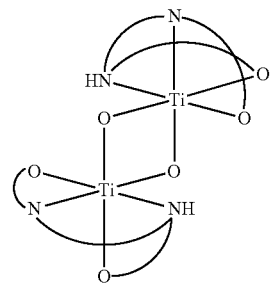

[wherein O—NH—N—O is represented by any of the following formulae (XXII), (XXII'), (XXIII), and (XXIII'):

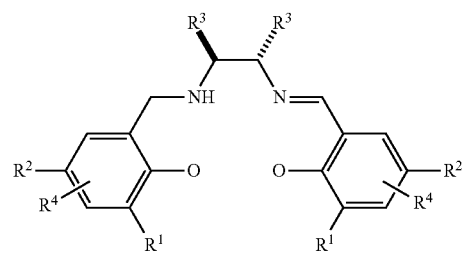

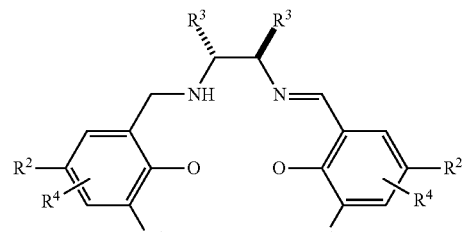

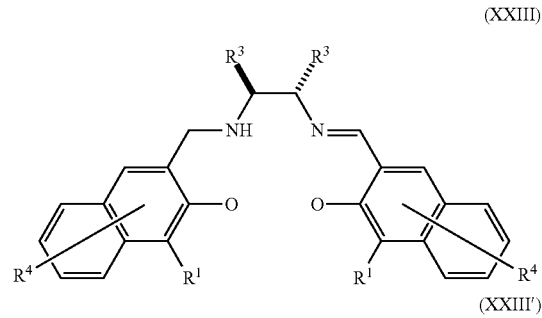

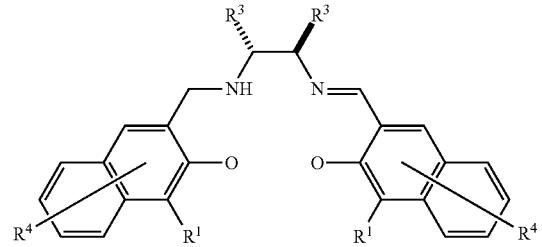

(wherein $R^1$, $R^2$, $R^3$, and $R^4$ are the same as above)] obtained by reducing one of the two imino bonds within the salen ligand.

Moreover, among the above-mentioned complexes is particularly preferable a titanium binuclear complex represented by the above formula (XXI) wherein O—NH—N—O in the formula is represented by the following formula (XXIV) or (XXIV'):

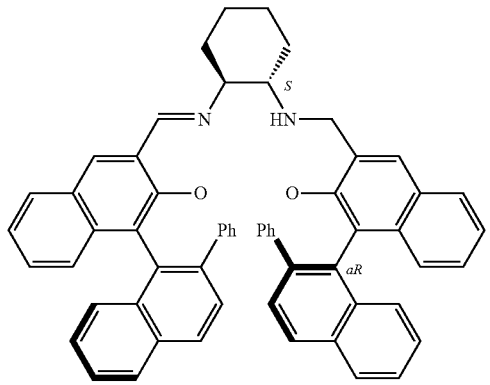

(XXIV)

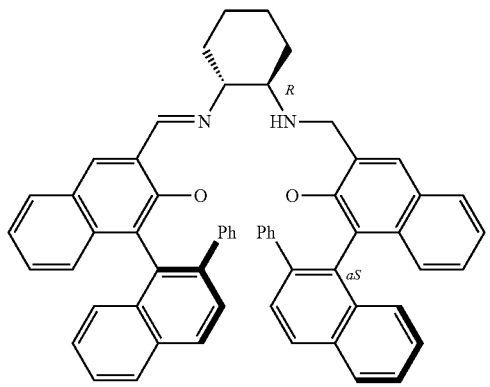

(XXIV')

{i.e. (Ars Δ, Ars Δ)-di-μ-oxo titanium binuclear complex, (Asr Λ, Asr Λ)-di-μ-oxo titanium binuclear complex}. These complexes are especially high in the stability, and can fully endure even in reaction conditions using hydrogen peroxide as an oxidant mentioned later.

The titanium binuclear complex represented by any of the above formulae (I), (I'), (III), and (III') wherein M is $TiY_2$ (wherein Y is μ-oxo ligand) can be produced by reacting the salen ligand represented by any of the above formulae (XVII), (XVII'), (XVIII), and (XVIII') with titanium alkoxide and then treating with water. In the reaction between the salen ligand and titanium alkoxide, one of the two imino bonds within the salen ligand is reduced by Meerwein-Ponndrof-Verley (MPV) reduction, and then self-assembled by treating with water to form the titanium binuclear complex. As the titanium alkoxide used are mentioned titanium tetramethoxide, titanium tetraethoxide, titanium tetrapropoxide, titanium tetraisopropoxide, titanium tetrabutoxide and the like, and among them, titanium tetraisopropoxide [$Ti(O^iPr)_4$] is preferable. Also, the ligand represented by the formula (XVIII) or (XVIII') is preferable as the salen ligands used. Furthermore, the amount of titanium alkoxide used is preferable to be within a range of 100~200 mol % per the molar quantity of the above-mentioned salen ligand. Moreover, the amount of water used is preferable to be within a range of 100~1000 mol % per the molar quantity of the above salen ligand. In the production method of the optically active epoxy compound according to the present invention, the above titanium binuclear complexes are produced in the reaction system and used for the asymmetric epoxidation of the unsaturated compound with an oxidant.

Also, the titanium binuclear complex represented by any of the above formulae (II), (II'), (IV) and (IV') wherein M is $TiY_2$ (wherein Y is a μ-oxo ligand) can be produced by reducing the salen ligand represented by any of the above formulae (XVII), (XVII'), (XVIII) and (XVIII') to produce the salan ligand represented by any of the above formulae (XIX), (XIX'), (XX) and (XX'), reacting this salan ligand with titanium alkoxide and then treating with water. Here, the reduction of the salen ligands can be conducted with a reducing agent such as $NaBH_4$ or the like. As the titanium alkoxide used are mentioned titanium tetramethoxide, titanium tetraethoxide, titanium tetrapropoxide, titanium tetraisopropoxide, titanium tetrabutoxide and the like, and among them, titanium tetraisopropoxide [$Ti(O^iPr)_4$] is preferable. Furthermore, the ligand represented by the above formulae (XVII) or (XVII') is preferable as the salen ligand used. Also, it is preferable that the amount of titanium alkoxide used is within a range of 100~200 mol % based on the molar quantity of the above salan ligand and the amount of water used is within a range of 100~1000 mol % based on the molar quantity of the above salan ligand. In the production method of the optically active epoxy compound according to the present invention, the above titanium binuclear complex is produced in the reaction system, which may be used for the asymmetric epoxidation of the unsaturated compound with the oxidant.

As the starting material in the production method of the optically active epoxy compound according to the present invention is used a prochiral compound having a carbon-carbon double bond in its molecule, i.e. the unsaturated compound represented by the above formula (V). Moreover, the epoxy compound produced by the method according to the present invention has a structure wherein the carbon-carbon double bond of the starting compound is converted into an epoxy bond or a structure represented by the above formula (VI). For example, when the compound represented by the above formula (VII) is used as the starting material, the resulting optically active epoxy compound is represented by the above formula (XIV), and when the compound represented by the above formula (VIII) is used as the starting material, the resulting optically active epoxy compound is represented by the above formula (XV), and when the compound represented by the above formula (IX) is used as the starting material, the resulting optically active epoxy compound is represented by the above formula (XVI).

In the above formulae (V) and (VI), $R^5$ and $R^6$ are not particularly limited as long as they are different monovalent groups or a hydrogen atom. In this case, a pair of enantiomers are existent in the resulting epoxy compound, but in the production method according to the present invention, just one of the enantiomers can be obtained with a high selectivity. Also, in the production method according to the present invention, both enantiomers of the optically active epoxy compounds can be obtained selectively by switching between complexes of the formulae (I) and (I'), the complexes of the formulae (II) and (II'), the complexes of the formulae (III) and (III'), and the complexes of the formulae (IV) and (IV').

In the above formulae (VII) and (XIV), $R^7$s are independently a hydrogen atom, a cyano group, a nitro group, an amino group which may be protected with a protecting group, a halogen atom, an alkyl group, an alkoxy group, a halogenoalkyl group, a carboxy group, a formyl group, an alkanoyl group, an aroyl group, a halogenoalkanoyl group, a carbamoyl group, an alkylsulfinyl group, an arylsulfinyl group, an alkylsulfonyl group, an arylsulfonyl group, an aminosulfonyl group, or a mono- or di-alkylaminosulfonyl group.

In the above $R^7$, as the amino group which may be protected with a protecting group are mentioned tosylamino group, benzylamino group, acylamino group, alkoxyamino group and the like. More concretely, as the acylamino group are mentioned acetylamino group, propionylamino group, benzoylamino group and the like, and as the alkoxyamino group are mentioned methoxycarbonylamino group, ethoxycarbonylamino group, n-propoxycarbonylamino group, i-propoxycarbonylamino group, n-butoxycarbonylamino group, i-butoxycarbonylamino group, sec-butoxycarbonylamino group, t-butoxycarbonylamino group and the like. Also, as the halogen atom are mentioned fluorine atom, chlorine atom, bromine atom and so on. As the alkyl group are preferable alkyl group having a carbon number of 1-4 such as methyl group, ethyl group, n-propyl group, i-propyl group, n-butyl group, i-butyl group, sec-butyl group, t-butyl group and the like. As the alkoxy group are preferable alkoxy groups having a carbon number of 1-4 such as methoxy group, ethoxy group, n-propoxy group, i-propoxy group, n-butoxy group, i-butoxy group, sec-butoxy group, and t-butoxy group. As the halogenalkyl group are preferable halogenoalkyl groups having a carbon number of 1-4 such as trifluoromethyl group, monochloromethyl group, and pentafluoroethyl group and the like. As the alkanoyl group are preferable alkanoyl groups having a carbon number of 1-4 such as acetyl group, propionyl group and the like. As the aroyl group are mentioned benzoyl group, o-toluoyl group, m-toluoyl group, p-toluoyl group, naphthoyl group and the like. As the halogenoalkanoyl group are preferable halogenoalkanoyl groups having a carbon number of 1-4 such as trifluoroacetyl group, monochloroacetyl group, pentafluoropropionyl group and the like. As the alkylsulfinyl group are preferable alkylsulfinyl groups having a carbon number of 1-4 such as methylsulfinyl group, ethylsulfinyl group, n-propylsulfinyl group, i-propylsulfinyl group, n-butylsulfinyl group, i-butylsulfinyl group, sec-butylsulfinyl group, t-butylsulfinyl group and the like. As the arylsulfinyl group are mentioned benzenesulfinyl group, o-toluenesulfinyl group, m-toluenesulfinyl group, p-toluenesulfinyl group and the like. As the alkylsulfonyl group are preferable alkylsulfonyl groups having a carbon number of 1-4 such as methylsulfonyl group, ethylsulfonyl group, n-propylsulfonyl group, i-propylsulfonyl group, n-butylsulfonyl group, i-butylsulfonyl group, sec-butylsulfonyl group, t-butylsulfonyl group and the like. As the arylsulfonyl group are mentioned benzenesulfonyl group, o-toluenesulfonyl group, m-toluenesulfonyl group, p-toluenesulfonyl group and the like. As the mono- or di-aslkylaminosulfonyl group are preferable mono- or di-alkylaminosulfonyl groups having a carbon number of 1-4 such as methylaminosulfonyl group, dimethylaminosulfonyl group, ethylaminosulfonyl group, diethylaminosulfonyl group, n-propylaminosulfonyl group, di-n-propylaminosulfonyl group and the like.

Also, $R^8$ in the above formulae (VII) and (XIV) is a hydrogen atom, an alkyl group, or an alkoxy group, and $R^9$s in the above formulae (VII), (VIII), (IX), (XIV), (XV) and (XVI) are independently a hydrogen atom, an alkyl group, an alkoxy group, a phenyl group or a substituted phenyl group substituted with a halogen atom, an alkyl group or an alkoxy group, provided that $R^9$s in the formulae (IX) and (XVI) are different from each other, and $R^8$ and $R^9$ in the formulae (VII) and (XIV) may be bonded with each other to form a bivalent group represented by any of the above formulae (X), (XI), (XII), and (XIII). In the formulae (X), (XI), (XII) and (XIII), $R^{10}$s are independently a hydrogen atom or an alkyl group, and as the alkyl group are preferable alkyl groups having a carbon number of 1-4 carbon atoms such as methyl group, ethyl group, n-propyl group, i-propyl group, n-butyl group, i-butyl group, sec-butyl group, t-butyl group and the like.

In the above $R^8$, alkyl groups having a carbon number of 1-4 such as methyl group, ethyl group, n-propyl group, i-propyl group, n-butyl group, i-butyl group, sec-butyl group, t-butyl group and the like are preferable as the alkyl group, and alkoxy groups having a carbon number of 1-4 such as methoxy group, ethoxy group, n-propoxy group, i-propoxy group, n-butoxy group, i-butoxy group, sec-butoxy group, t-butoxy group and the like are preferable as the alkoxy group. Also, in the above $R^9$, alkyl groups having a carbon number of 1-20 such as methyl group, ethyl group, n-propyl group, i-propyl group, n-butyl group, i-butyl group, sec-butyl group, t-butyl group, pentyl group, isopentyl group, neopentyl group, hexyl group, heptyl group, octyl group, 2-ethylhexyl group, nonyl group, decyl group, undecyl group, dodecyl group, tridecyl group, isotridecyl group, myristyl group, palmityl group, stearyl group, icosyl group, dococyl group and the like are preferable as the alkyl group, and alkoxy groups having a carbon number of 1-4 such as methoxy group, ethoxy group, n-propoxy group, i-propoxy group, n-butoxy group, i-butoxy group, sec-butoxy group, t-butoxy group and the like are preferable as the alkoxy group. Furthermore, in $R^9$, substituted phenyl groups substituted with a halogen atom, an alkyl group having a carbon number of 1-4 or an alkoxy group having a carbon number of 1-4 such as fluorophenyl group, chlorophenyl group, bromophenyl group, tolyl group, ethylphenyl group, t-butylphenyl group, 3,5-dimethylphenyl group, o-methoxyphenyl group, m-methoxyphenyl group, p-methoxyphenyl group and the like are preferable as the substituted phenyl group substituted with the halogen atom, alkyl group or alkoxy group.

Also, the above $R^8$ and $R^9$ may be bonded with each other to form a bivalent group. When $R^8$ and $R^9$ are bonded with each other to form a group represented by the above formula (X), a six-membered ring is formed, and as such a compound are mentioned benzopyran and its derivatives. Also, when $R^8$ and $R^9$ are bonded with each other to form a group represented by the above formula (XI), a five-membered ring is formed, and as such a compound are mentioned indene and its derivatives. Moreover, when $R^8$ and $R^9$ are bonded with each other to form a group represented by the above formula (XII), a six-membered ring is formed, and as such a compound are mentioned 1,2-dihydronaphthalene and its derivatives. Furthermore, when $R^8$ and $R^9$ bond with each other to form a group represented by the above formula (XIII), a seven-membered ring is formed, and as such a compound are mentioned 6,7-dihydro-5H-benzo-cycloheptene and its derivatives.

Aqueous hydrogen peroxide or urea-hydrogen peroxide adduct (UHP) is preferable as the oxidant used in the method according to the prevent invention, and aqueous hydrogen peroxide is especially preferable. Here, the concentration of the aqueous hydrogen peroxide is not particularly limited, but it is preferable to use commercially available one having a concentration of about 30% in view of the safety, industrial viewpoints and easiness of acquisition. Also the aqueous hydrogen peroxide may be dripped little by little, and in this case, the amount of catalysts used can be reduced. Moreover, the amount of the oxidant used is preferably within a range of 1-10 equivalents (eq) relative to the unsaturated compound as the substrate, more preferably within a range of 1-1.2 equivalents (eq).

The production method according to the present invention is generally carried out in an organic solvent. As the organic solvent is preferable a non-protonic solvent, which concretely includes a halogenated hydrocarbon such as dichloromethane ($CH_2Cl_2$) or the like; an aromatic hydrocarbon such as toluene or the like; an ester such as ethyl acetate or the like; and an ether such as tetrahydrofuran (THF) or the like.

The production method according to the present invention is not specifically limited, but it is preferable that the method is carried out at 0-50° C., more preferably at room temperature. The enantiomer excess of the product lowers when the reaction temperature is either too high or too low. In addition, the reaction time is not particularly limited, and is selected appropriately in accordance with the above reaction temperature.

EXAMPLES

The following examples are given in illustration of the invention, but are not intended as limitations thereof.

Synthesis Example of Complex 1

A compound represented by the following formula (XXV) (826.8 mg, 1.0 mmol):

(XXV)

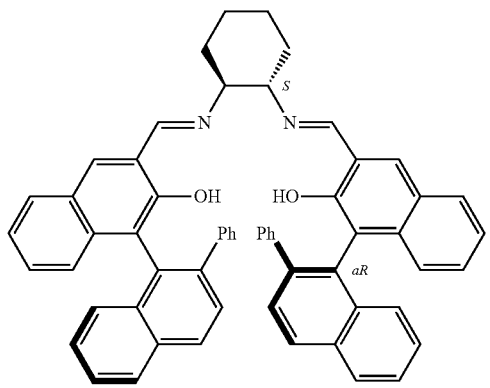

and $Ti(O^iPr)_4$ (568.2 mg, 2.0 mmol) are dissolved in dichloromethane (4.0 ml), and the resulting solution is stirred at room temperature for three days, and thereafter added with water (36 mg, 2.0 mmol), and further stirred at room temperature for two hours. The resulting yellow precipitates are obtained by filtering with a glass filter. The filtered raw product is recrystallized from dichloromethane/diethylether to obtain a (Ars Δ, Ars Δ)-di-μ-oxo titanium binuclear complex (complex 1) (343.2 mg, 39% yield) represented by the above formula (XXI) wherein O—NH—N—O is the above formula (XXIV). The result of the elemental analysis of the obtained compound is C, 79.65; H, 5.20; N, 3.11, which are well accorded with the calculated values of $C_{120}H_{92}N_4O_6Ti_2 \cdot 1.5H_2O$ (C, 79.68; H, 5.29; N, 3.10). As a result of the X-ray structure analysis of the obtained complex, the length of in-plane C—N bond is 1.276 Å and 1.265 Å, and the length of out-of-plane C—N bond is 1.492 Å and 1.496 Å.

Synthesis Example of Complex 2

A compound represented by the following formula (XXVI) (827.0 mg, 1.0 mmol)

(XXVI)

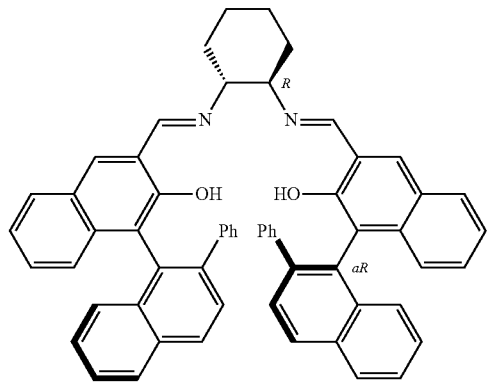

and $Ti(O^iPr)_4$ (568.2 mg, 2.0 mmol) are dissolved in dichloromethane (4.0 ml), and the resulting solution is stirred at room temperature for three days, and thereafter added with water (100 mg, 5.5 mmol) and further stirred at room temperature for two hours. After the solvent is distilled off under a reduced pressure, the recrystallization is carried out from dichloromethane/heptane to obtain a (Arr Δ, Arr Λ)-di-μ-oxo titanium binuclear complex (complex 2) (180.5 mg, 20% yield) represented by the following formula (XXVII) wherein O—NH—N—O is represented by the following formula (XXVIII). The result of the elemental analysis of the obtained compound is C, 79.37; H, 5.35; N, 3.07, which are well accorded with the calculated value of $C_{120}H_{92}N_4O_6Ti_2 \cdot 2H_2O$ (C, 79.29; H, 5.32; N, 3.08). As a result of the X-ray structure analysis of the obtained complex, the length of in-plane C—N bond is 1.271 Å and 1.266 Å, and the length of out-of-plane C—N bond is 1.490 Å and 1.497 Å. Moreover, the result of the high resolution FAB mass spectrum analysis using JEOL MX-SX/SX 102 Åspectrometer and m-nitrobenzylalcohol is m/Z=1780.6, which is well accorded with the theoretical value of $[C_{120}H_{92}N_4O_6Ti_2]^+$.

(XXVII)

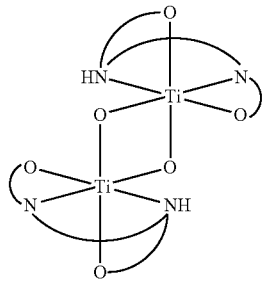

(XXVIII)

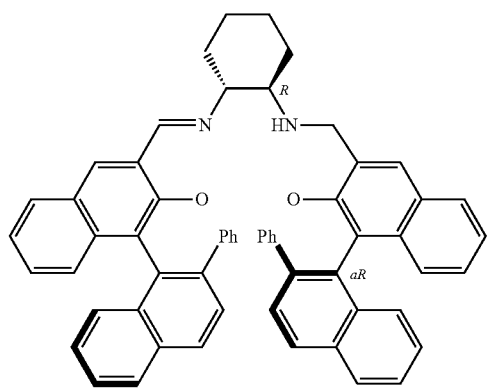

Synthesis Example of Complex 3

A salen ligand represented by the following formula (XXIX) is reduced with NaBH$_4$ to produce a salan ligand represented by the following formula (XXX), and Ti(O$^i$Pr)$_4$ (1.02 mmol) is added to a dichloromethane solution (2.0 Ml) of the salan ligand (0.86 mmol) represented by the formula (XXX), and stirred at room temperature overnight. After few drops of water are added, the resulting mixed solution is further stirred overnight. After the solvent is distilled off under a reduced pressure, a di-μ-oxo titanium (salan) complex (complex 3) (65% yield) represented by the following formula (XXXI) is obtained through recrystallization from dichloromethane. The result of the elemental analysis of the obtained compound is C, 70.21; H, 9.43; N, 4.31, which are well accorded with the calculated value of C$_{72}$H$_{112}$N$_4$O$_6$Ti$_2$.0.5H$_2$O(C, 70.05; H, 9.23; N, 4.54).

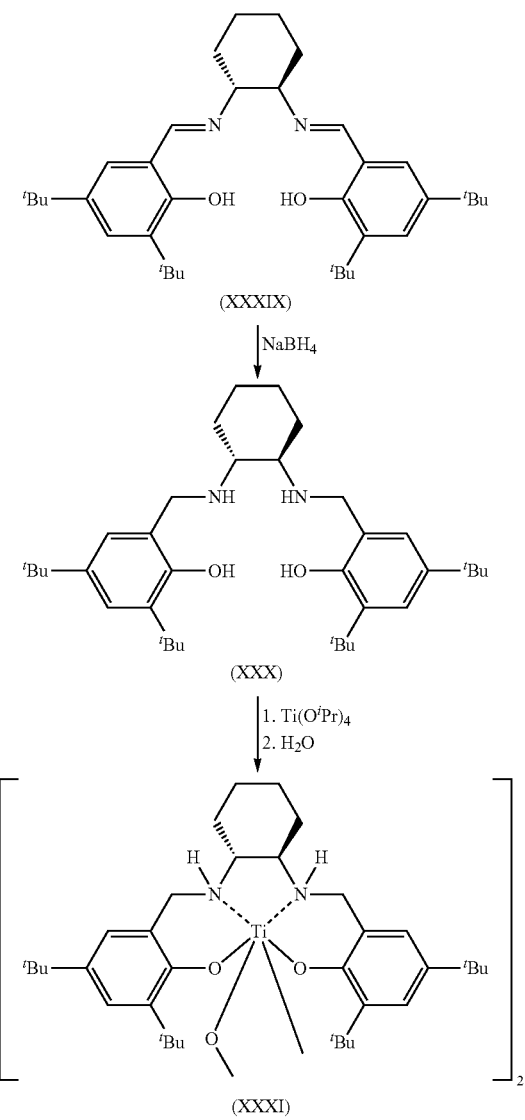

(XXXIX)

(XXX)

(XXXI)

Synthesis Example of Complex 4

A salen ligand represented by the following formula (XXXII) is reduced with NaBH$_4$ to produce a salan ligand represented by the following formula (XXXIII), and Ti(O$^i$Pr)$_4$ (1.33 mmol) is added to a dichloromethane solution (3.5 Ml) of the salan ligand (1.20 mmol) represented by the formula (XXXIII), and stirred at room temperature for five hours. After few drops of water are added, the resulting mixed solution is further stirred overnight. After the solvent is distilled off under a reduced pressure, a di-μ-oxo titanium (salan) complex (complex 4) (46% yield) represented by the following formula (XXXIV) is obtained through recrystallization from dichloromethane. The infrared spectrum of the obtained compound is IR (KBr): 3427, 3225, 3055, 2932, 2856, 1587, 1454, 1425 cm$^{-1}$.

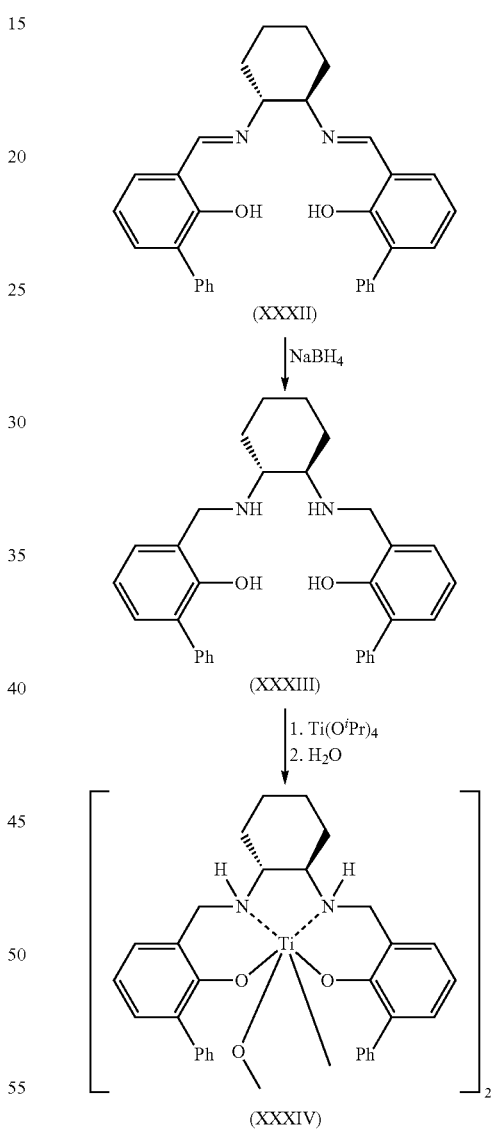

(XXXII)

(XXXIII)

(XXXIV)

Example 1

The complex 1 (3.6 mg, 0.002 mmol) represented by the above formula (XXI) wherein O—NH—N—O is represented by the above formula (XXIV) is dissolved in dichloromethane (2.0 ml). To the resulting solution are continuously added a substrate 1 (26.0 mg, 0.20 mmol) and 30% aqueous hydrogen peroxide (22.7 mg, 0.20 mmol) and reacted by stirring at room temperature (25° C.) for twelve hours. Thereafter, the mixed solution is concentrated under a reduced pressure and separated through a chromatograph with silica gel using a mixed solution of pentane:diethylether (40:1) to obtain a product 1.

Example 2

The complex 1 (1.2 mg, 0.00067 mmol) represented by the above formula (XXI) wherein O—NH—N—O is represented by the above formula (XXIV) is dissolved in dichloromethane (2.0 ml). To the resulting solution are continuously added a substrate 1 (86.7 mg, 0.67 mmol) and 30% aqueous hydrogen peroxide (76.0 mg, 0.67 mmol) and reacted by stirring at room temperature (25° C.) for 72 hours. Thereafter, the mixed solution is concentrated under a reduced pressure and separated through a chromatograph with silica gel using a mixed solution of pentane:diethylether (40:1) to obtain a product 1.

Examples 3~4

The reaction is performed in the same manner as in Example 1 except that toluene or ethyl acetate is used as a solvent instead of dichloromethane. However, the reaction time is 18 hours.

Example 5

The reaction is performed in the same way as in Example 1 except that tetrahydrofuran (THE) is used as a solvent instead of dichloromethane. However, the reaction time is 85 hours.

Examples 6~9

The reaction is performed in the same way as in Example 4 except that a substrate 2, substrate 3, substrate 4 or substrate 5 is used instead of the substrate 1. However, the reaction time is 24 hours.

Example 10

The complex 2 (5.3 mg, 0.003 mmol) represented by the above formula (XXVII) wherein O—NH—N—O is represented by the above formula (XXVIII) is dissolved in dichloromethane (3.0 ml). To the resulting solution are continuously added the substrate 1 (39.1 mg, 0.30 mmol) and urea-hydrogen peroxide adduct (33.9 mg, 0.36 mmol) and reacted by stirring at room temperature (25° C.) for 24 hours. Thereafter, the mixed solution is concentrated under a reduced pressure and separated through a chromatograph with silica gel using a mixed solution of pentane:diethylether (40:1) to obtain a product 1 (6.1 mg, 0.042 mmol).

Example 11

The reaction is performed in the same way as in Example 10 except that the substrate 2 is used instead of the substrate 1.

The above results are shown in Table 1. Moreover, the yield of the product in Examples 1~8 is analyzed by $^1$H-NMR (400 MHz). As a result, products other than the epoxy compound are not confirmed. In Table 1, the enantiomer excess of the product is analyzed through a high performance liquid chromatography (HPLC) using Daicel chiralcel OB-H and hexane/isopropanol (99/1) mixture for product 1, Daicel chiralpak AS-H and hexane/isopropanol (99.9/0.1) mixture for product 2, Daicel chiralcel OD-H and hexane/isopropanol (99/1) mixture for product 3, and Daicel chiralcel OD-H and hexane/isopropanol (99.9/0.1) mixture for product 4, respectively.

TABLE 1

| | Substrate *2 | Catalyst | | | | | Product *2 | | Enantiomer |
| | (Unsaturated compound) | Type | Amount used (mol %) *1 | Oxidant | Solvent | Reaction time (hr) | (Epoxy Compound) | Yield (%) | excess (% ee) |
|---|---|---|---|---|---|---|---|---|---|
| Example 1 | Substrate 1 | Complex 1 | 1 | $H_2O_2$ | $CH_2Cl_2$ | 12 | Product 1 | 100 | <99 |
| Example 2 | Substrate 1 | Complex 1 | 0.1 | $H_2O_2$ | $CH_2Cl_2$ | 72 | Product 1 | 100 | <99 |
| Example 3 | Substrate 1 | Complex 1 | 1 | $H_2O_2$ | Toluene | 18 | Product 1 | 100 | <99 |
| Example 4 | Substrate 1 | Complex 1 | 1 | $H_2O_2$ | Ethyl acetate | 18 | Product 1 | 100 | <99 |
| Example 5 | Substrate 1 | Complex 1 | 1 | $H_2O_2$ | THF | 85 | Product 1 | 97 | 97 |
| Example 6 | Substrate 2 | Complex 1 | 1 | $H_2O_2$ | Ethyl acetate | 24 | Product 2 | 100 | 96 |
| Example 7 | Substrate 3 | Complex 1 | 1 | $H_2O_2$ | Ethyl acetate | 24 | Product 3 | 93 | 83 |
| Example 8 | Substrate 4 | Complex 1 | 1 | $H_2O_2$ | Ethyl acetate | 24 | Product 4 | 73 | 94 |
| Example 9 | Substrate 5 | Complex 1 | 1 | $H_2O_2$ | Ethyl acetate | 24 | Product 5 | 69 | 82 |
| Example 10 | Substrate 1 | Complex 2 | 1 | UHP | $CH_2Cl_2$ | 24 | Product 1 | 14 | 83 |
| Example 11 | Substrate 2 | Complex 2 | 1 | UHP | $CH_2Cl_2$ | 24 | Product 2 | 7 | 82 |

*1 Amount of catalyst used with respect to the unsaturated compound as a substrate.
*2 Structures of substrates and products are shown below.

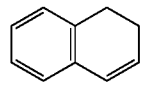

Substrate 1

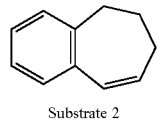

Substrate 2

TABLE 1-continued

| Substrate *2 (Unsaturated compound) | Catalyst | | Oxidant | Solvent | Reaction time (hr) | Product *2 (Epoxy Compound) | Yield (%) | Enantiomer excess (% ee) |
|---|---|---|---|---|---|---|---|---|
| | Type | Amount used (mol %) *1 | | | | | | |

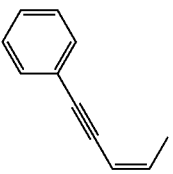
Substrate 3

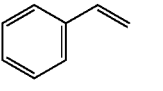
Substrate 4

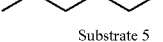
Substrate 5

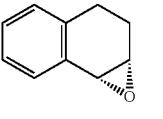
Product 1

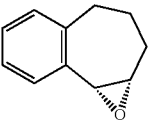
Product 2

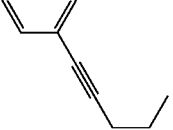
Product 3

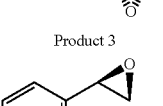
Product 4

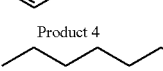
Product 5

As seen from Table 1, optically active epoxy compounds can be produced by asymmetrically epoxidizing various unsaturated compounds using complexes which have salalen ligands produced by reducing one of the two imino bonds within the salen ligand as a catalyst.

Example 12

The complex 3 (5 μmol) represented by the above formula (XXXI) and the substrate 1 (0.1 mmol) are dissolved in dichloromethane (1.0 ml). To the resulting solution is added 30% aqueous hydrogen peroxide (0.12 mmol) and reacted by stirring at room temperature (25° C.) for 24 hours. Thereafter, the solvent is distilled off under a reduced pressure, and the residue is separated through a chromatograph with silica gel using a mixed solution of pentane:diethylether (40:1) to obtain a product 1.

Example 13

The reaction is performed in the same way as in Example 12 except that the complex 4 (5 mol) represented by formula (XXXIV) is used instead of the complex 3 (5 mop represented by formula (XXXI) and the reaction time is 8 hours.

Example 14

The reaction is performed in the same way as in Example 13 except that the reaction temperature is 0° C. and the reaction time is 24 hours.

Example 15

The reaction is performed in the same way as in Example 14 except that the amount of 30% aqueous hydrogen peroxide used is 0.15 mmol.

Example 16

Salan ligands represented by formula (XXXIII) (10 μmol) is added to a dichloromethane solution of Ti(O$^i$Pr)$_4$ (1.0 Ml, 10 Mm) and then stirred at room temperature. After 30 minutes, one drop of water is added and further stirred for 30 minutes. Next, the substrate 1 (0.1 mmol) and 30% aqueous hydrogen peroxide (0.12 mmol) are added and reacted by stirring at room temperature (25° C.) for 6 hours. Thereafter, the solvent is distilled off under a reduced pressure, and the residue is separated through a chromatograph with silica gel using a mixed solution of pentane:diethylether (40:1) to obtain a product 1.

Examples 17~22

The reaction is performed in the same way as in Example 15 except that a substrate 6, substrate 2, substrate 4, substrate 7, substrate 8 or substrate 5 is used instead of the substrate 1 and the reaction temperature is 25° C.

The above results are shown in Table 2. Moreover, the yield of the product is analyzed by $^1$H-NMR (400 MHz). As a result, products other than the epoxy compound are not confirmed. In Table 2, the enantiomer excess of the product is analyzed through a high performance liquid chromatography (HPLC) using Daicel chiralcel OB-H and hexane/isopropanol (99/1) mixture for product 1, Daicel chiralcel OB-H and hexane/isopropanol (90/10) mixture for product 6, Daicel chiralpak and hexane/isopropanol (99.9/0.1) mixture for product 2, Daicel chiralcel OD-H and hexane/isopropanol (99.9/0.1) mixture for product 4, Daicel chiralcel OJ-H and hexane/isopropanol (99.9/0.1) mixture for product 7, and Daicel chiralcel OB-H and hexane/isopropanol (99/1) mixture for product 8, respectively. Furthermore, the enantiomer excess of product 5 is analyzed by $^1$H-NMR with chiralshift reagent Eu(hfc)$_3$.

TABLE 2

|  | Substrate *3 (Unsaturated compound) | Catalyst | Amount of H$_2$O$_2$ used (mmol %) | Reaction time (hr) | Reaction temperature (° C.) | Product *3 (Epoxy compound) | Yield (%) | Enantiomer excess (% ee) |
|---|---|---|---|---|---|---|---|---|
| Example 12 | Substrate 1 | Complex 3 | 0.12 | 24 | 25 | Product 1 | 19 | 82 |
| Example 13 | Substrate 1 | Complex 4 | 0.12 | 8 | 25 | Product 1 | 75 | 96 |
| Example 14 | Substrate 1 | Complex 4 | 0.12 | 24 | 0 | Product 1 | 59 | 97 |
| Example 15 | Substrate 1 | Complex 4 | 0.15 | 24 | 0 | Product 1 | 79 | 98 |
| Example 16 | Substrate 1 | Complex 4 *4 | 0.12 | 6 | 25 | Product 1 | 90 | 95 |
| Example 17 | Substrate 6 | Complex 4 | 0.15 | 24 | 25 | Product 6 | 72 | 95 |
| Example 18 | Substrate 2 | Complex 4 | 0.15 | 24 | 25 | Product 2 | 44 | 97 |
| Example 19 | Substrate 4 | Complex 4 | 0.15 | 24 | 25 | Product 4 | 47 | 82 |
| Example 20 | Substrate 7 | Complex 4 | 0.15 | 24 | 25 | Product 7 | 72 | 73 |
| Example 21 | Substrate 8 | Complex 4 | 0.15 | 24 | 25 | Product 8 | 55 | 95 |
| Example 22 | Substrate 5 | Complex 4 | 0.15 | 24 | 25 | Product 5 | 8 | 55 |

*3 Substrate 1, substrate 2, substrate 4, substrate 5, product 1, product 2, product 4, and product 5 are the same as in Table 1. Structures of substrate 6, substrate 7, substrate 8, product 6, product 7, and product 8 are shown below.
*4 Catalyst 4 is synthesized in situ.

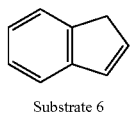

Substrate 6

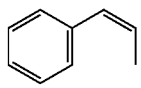

Substrate 7

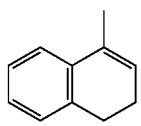

Substrate 8

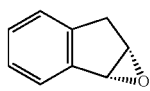

Product 6

TABLE 2-continued

| Substrate *3 (Unsaturated compound) | Catalyst | Amount of H₂O₂ used (mmol %) | Reaction time (hr) | Reaction temperature (° C.) | Product *3 (Epoxy compound) | Yield (%) | Enantiomer excess (% ee) |
| --- | --- | --- | --- | --- | --- | --- | --- |

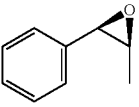

Product 7

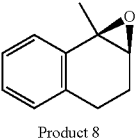

Product 8

As seen from Table 2, optically active epoxy compounds can be produced by asymmetrically epoxidizing various unsaturated compounds using complexes which have salan ligands produced by reducing both of the two imino bonds within the salen ligand as a catalyst.

INDUSTRIAL APPLICABILITY

The production method according to the present invention is very useful for producing optically active epoxy compounds by epoxidizing prochiral unsaturated compounds having a carbon-carbon double bond in their molecule with a high enantioselectivity. Also, the complexes according to the present invention are very useful as a catalyst for this production method. Moreover, the optically active epoxy compounds obtained by the production method according to the present invention are useful as an intermediate for various drugs including optically active benzopyran compounds effective for the treatment of hypertension, asthma and the like.

What is claimed is:

1. A complex represented by any of the following formulae (I), (I'), (II), (II'), (III), (III'), (IV), and (IV'):

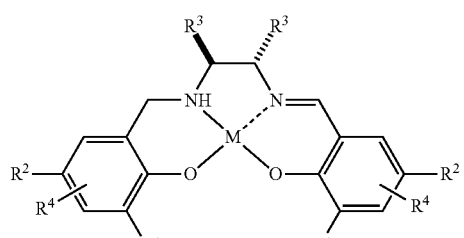

(I)

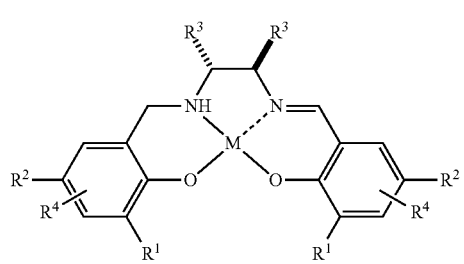

(I')

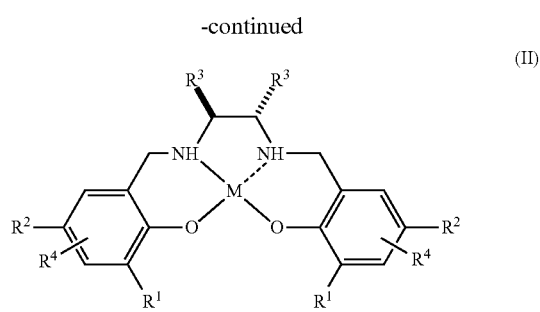

(II)

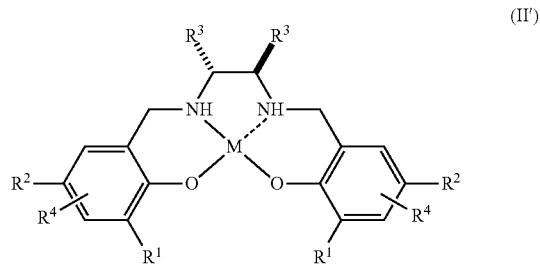

(II')

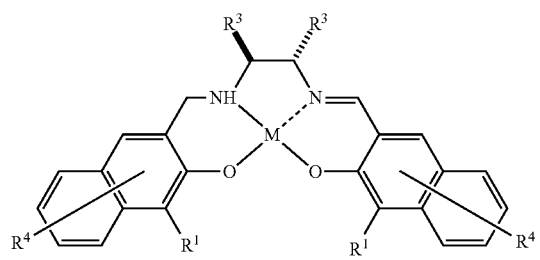

(III)

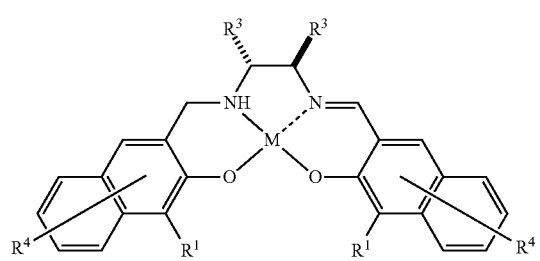

(III')

-continued (IV)

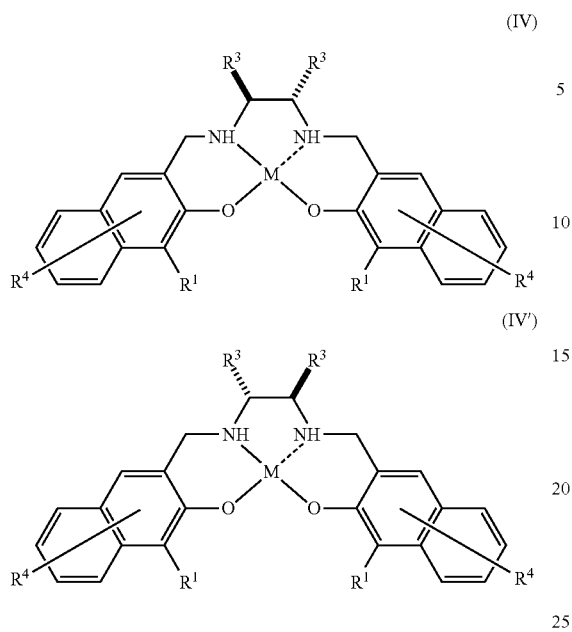

(IV')

wherein:

R¹s are independently an alkyl group or an aryl group;

R²s are independently a hydrogen atom, an alkyl group or an aryl group;

R³s are independently an alkyl group or an aryl group, provided that two R³s are optionally bonded with each other to form a ring;

R⁴s are independently a hydrogen atom, a halogen atom, an alkyl group, an alkoxy group, a nitro group or a cyano group; and M is $TiY_2$, wherein Y is Cl or alkoxide or the complex forms a di-μ-oxo dimer where Y is a μ-oxo ligand.

2. The complex according to claim 1, wherein the two R³s in formulae (I), (I'), (II), (II'), (III), (III'), (IV), and (IV') are bonded with each other to form a tetramethylene group.

3. The complex according to claim 1, wherein the complex is represented by formulae (II), (II'), (III), or (III').

4. The complex according to claim 1, wherein R¹ in formulae (I), (I'), (II), (II'), (III), (III'), (IV), and (IV') is an aryl group.

5. The complex according to claim 1, wherein Y is a μ-oxo ligand.

6. A process for producing a complex represented by any of the following formulae (I), (I'), (III), and (III'):

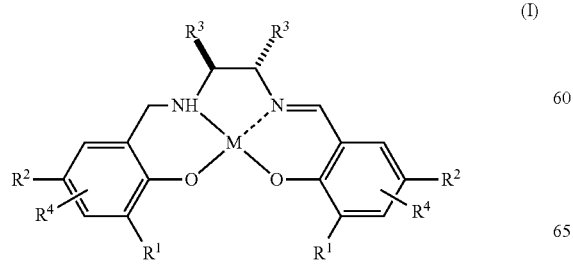

-continued

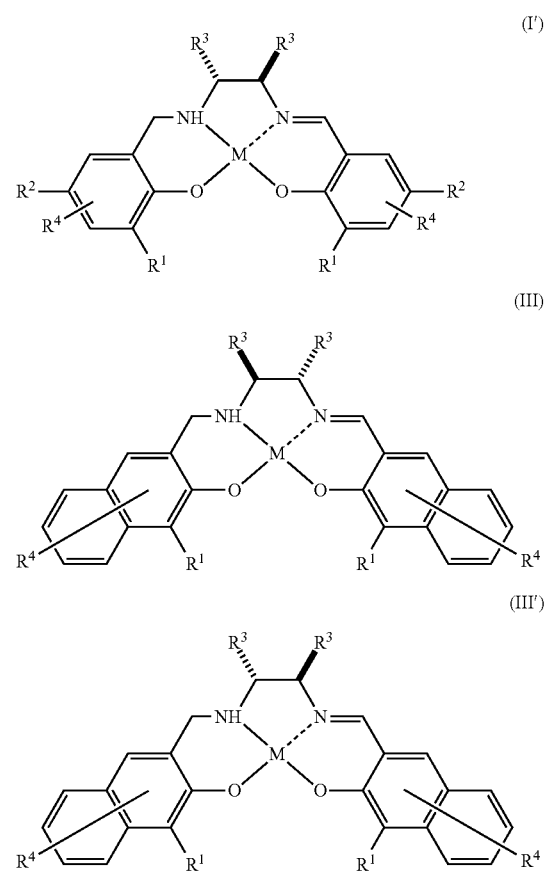

the process comprising:

reacting with titanium alkoxide a salen ligand represented by any of the following formulae (XVII), (XVII'), (XVIII), and (XVIII'):

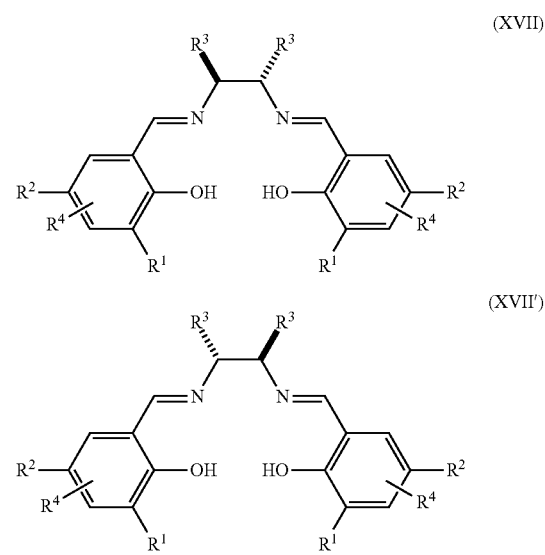

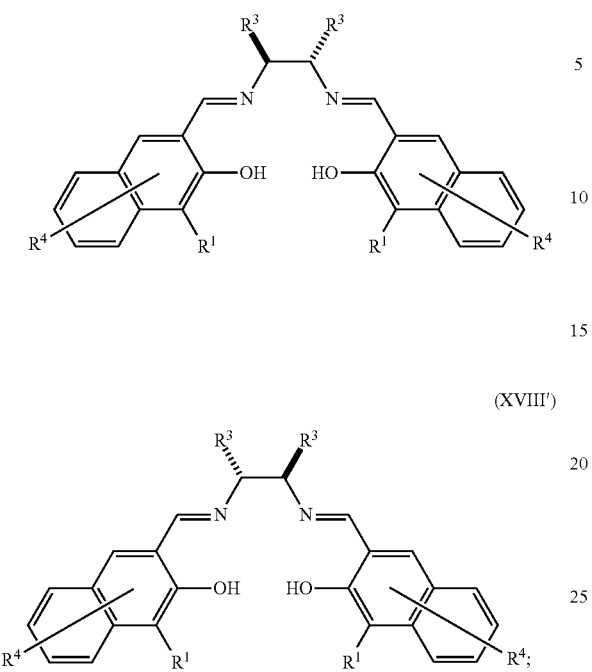

and treating the reacted salen ligand with water to produce the complex represented by any of the formulae (I), (I'), (III), and (III'), wherein:

$R^1$s are independently an alkyl group or an aryl group;

$R^2$s are independently a hydrogen atom, an alkyl group or an aryl group;

$R^3$s are independently an alkyl group or an aryl group, provided that two $R^3$s are optionally bonded with each other to form a ring;

$R^4$s are independently a hydrogen atom, a halogen atom, an alkyl group, an alkoxy group, a nitro group or a cyano group; and M is $TiY_2$, wherein the complex forms a di-μ-oxo dimer where Y is a μ-oxo ligand.

7. The process for producing a complex according to claim 6, wherein the two $R^3$s in formulae (I), (I'), (III), (III'), (XVII), (XVII'), (XVIII), and (XVIII') are bonded with each other to form a tetramethylene group.

8. The process for producing a complex according to claim 6, wherein the salen ligand is represented by formulae (XVIII) or (XVIII') and the complex is represented by formulae (III) or (III').

9. The process for producing a complex according to claim 6, wherein $R^1$ in formulae (I), (I'), (III), (III'), (XVII), (XVII'), (XVIII), and (XVIII') is an aryl group.

10. A process for producing a complex represented by any of the following formulae (II), (II'), (IV), and (IV'):

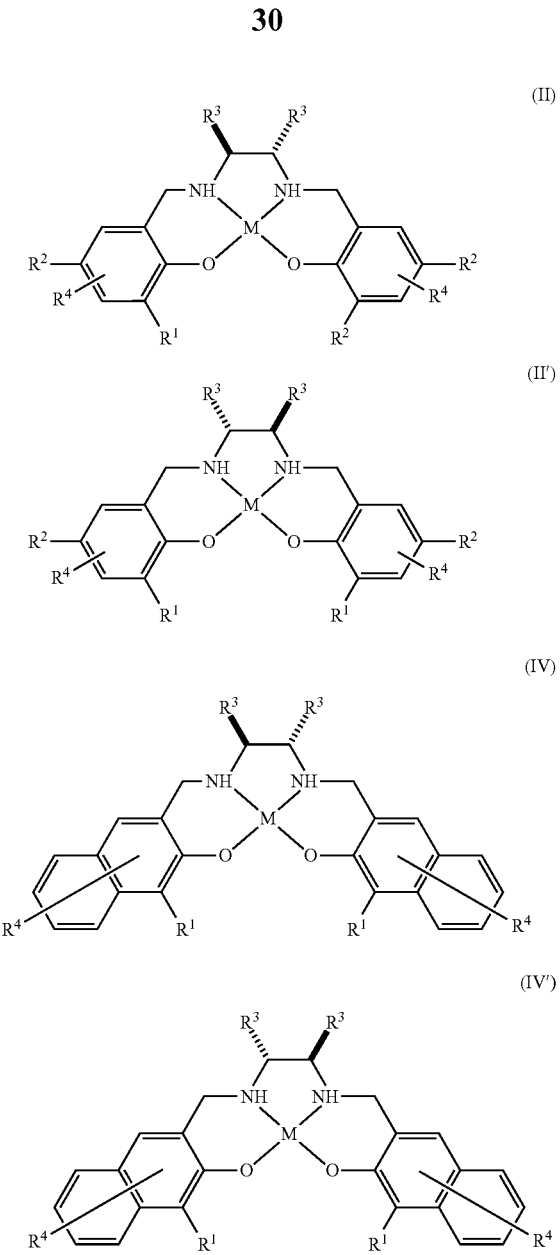

the process comprising:

reducing a salen ligand represented by any of the following formulae (XVII), (XVII'), (XVIII), and (XVIII'):

-continued (XVII′)

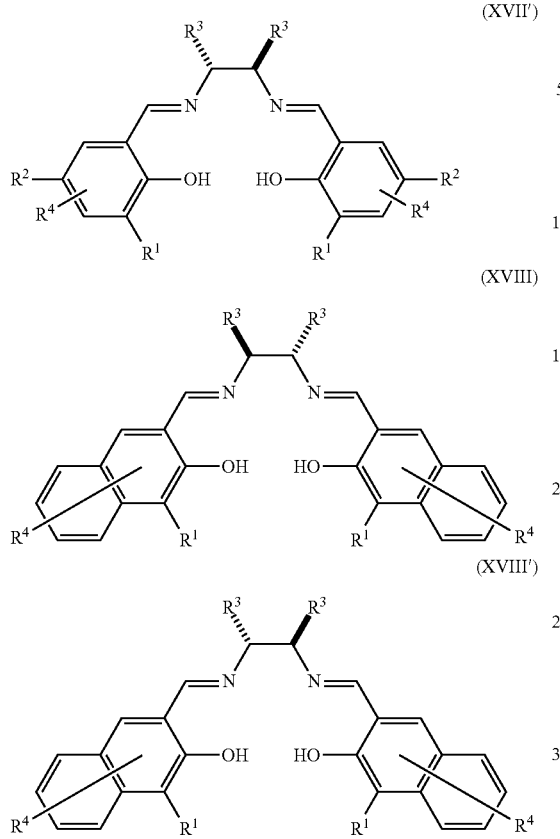

(XVIII)

(XVIII′)

to form a salan ligand represented by any of the following formulae (XIX), (XIX′), (XX), and (XX′):

(XIX)

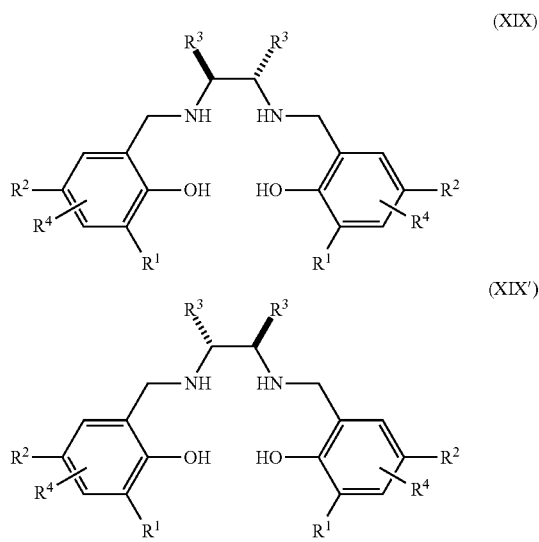

(XIX′)

-continued (XX)

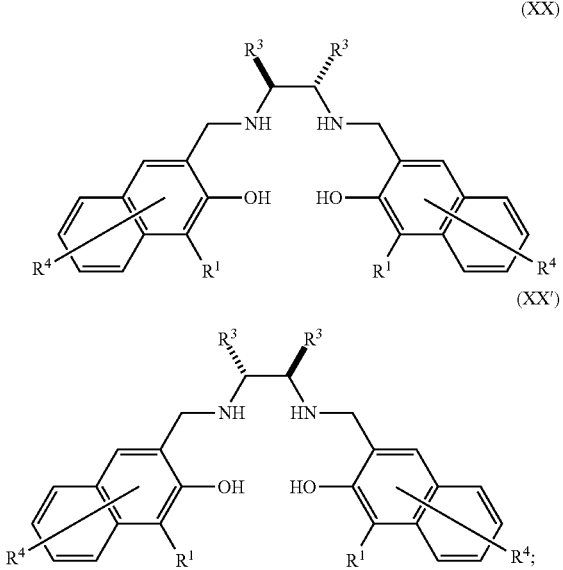

(XX′)

reacting the salan ligand with titanium alkoxide; and
treating the reacted salan ligand with water to produce the complex represented by any of the formulae (II), (II′), (IV), and (IV′), wherein:

$R^1$s are independently an alkyl group or an aryl group;

$R^2$s are independently a hydrogen atom, an alkyl group or an aryl group;

$R^3$s are independently an alkyl group or an aryl group, provided that two $R^3$s are optionally bonded with each other to form a ring;

$R^4$ are independently a hydrogen atom, a halogen atom, an alkyl group, an alkoxy group, a nitro group or a cyano group; and M is $TiY_2$, wherein the complex forms a di-μ-oxo dimer where Y is a μ-oxo ligand.

11. The process for producing a complex according to claim 10, wherein the two $R^3$s in formulae (II), (II′), (IV), (IV′), (XVII), (XVII′), (XVIII), (XVIII′), (XIX), (XIX′), (XX), and (XX′) are bonded with each other to form a tetramethylene group.

12. The process for producing a complex according to claim 10, wherein the salen ligand is represented by the formulae (XVII) or (XVII′), and the salan ligand is represented by formulae (XIX) or (XIX′), and the complex is represented by formulae (II) or (II′).

13. The process for producing a complex according to claim 10, wherein $R^1$ in formulae (II), (II′), (IV), (IV′), (XVII), (XVII′), (XVIII), (XVIII′), (XIX), (XIX′), (XX), and (XX′) is an aryl group.

* * * * *